United States Patent [19]

Nastke et al.

[11] Patent Number: 5,662,916
[45] Date of Patent: Sep. 2, 1997

[54] PESTICIDAL FORMULATIONS

[75] Inventors: Rudolf Nastke, Rehbrülke; Andreas Leonhardt, Freiburg, both of Germany; Ernst Neuenschwander, Riehen, Switzerland

[73] Assignee: Ciba-Geigy Corporation, Tarrytown, N.Y.

[21] Appl. No.: 451,690

[22] Filed: May 26, 1995

Related U.S. Application Data

[63] Continuation of Ser. No. 193,815, Feb. 9, 1994, abandoned, which is a continuation of Ser. No. 941,586, Sep. 8, 1992, abandoned.

[30] Foreign Application Priority Data

Sep. 11, 1991 [CH] Switzerland .................. 2670/91

[51] Int. Cl.⁶ ........................................ A01N 25/28
[52] U.S. Cl. .................. 424/408; 424/417; 427/213.36; 264/433; 264/46
[58] Field of Search .................................. 424/408, 417; 427/213.36; 264/4.33, 4.6

[56] References Cited

U.S. PATENT DOCUMENTS

| | | | |
|---|---|---|---|
| 3,516,846 | 6/1970 | Matson | 424/497 |
| 3,778,383 | 12/1973 | Schibler et al. | 232/316 |
| 3,919,110 | 11/1975 | Vassiliades | 252/316 |
| 3,981,821 | 9/1976 | Kiritani et al. | 252/316 |
| 4,001,140 | 1/1977 | Foris et al. | 252/316 |
| 4,157,983 | 6/1979 | Golden | 252/316 |
| 4,219,604 | 8/1980 | Kakimi et al. | 428/307 |
| 4,557,755 | 12/1985 | Takahashi et al. | |
| 4,696,822 | 9/1987 | Matsumura | 424/490 |
| 4,889,719 | 12/1989 | Ohtsubo | 424/408 |
| 5,061,410 | 10/1991 | Sakamoto et al. | 264/4.7 |

FOREIGN PATENT DOCUMENTS 0397325  11/1990  European Pat. Off. .
WO91/04661  of 0000  WIPO .

OTHER PUBLICATIONS

Derwent Abstract 90-049214/07 (of JP 146257) Jun. 14, 1988.

*Primary Examiner*—Jyothsna Venkat
*Attorney, Agent, or Firm*—Marla J. Mathias; William A. Teoli, Jr.

[57] ABSTRACT

The invention relates to a novel formulation of per se known pesticides in the form of microcapsules, to a process for the preparation of microcapsules and to the use of said microcapsules for controlling weeds, plant diseases, insects and representatives of the order Acarina.

4 Claims, No Drawings

PESTICIDAL FORMULATIONS

This application is a continuation of application Ser. No. 08/193,815, filed Feb. 9, 1994, now abandoned, which is a continuation of application Ser. No. 07/941,586, filed Sep. 8, 1992, now abandoned.

The present invention relates to a novel formulation in the form of microcapsules of per se known pesticides, to a process for the preparation of microcapsules, and to the use of said microcapsules for controlling weeds, plant diseases, insects and representatives of the order Acarina.

The preparation of pesticidal formulations by reacting urea with formaldehyde in the molar ratio of urea to formaldehyde of 1.35:1 to 1:2 in aqueous medium and subsequently stirring the precondensate into an acidified aqueous dispersion of the pesticide is disclosed in U.S. Pat. No. 3,516,846. However, the formulations prepared in accordance with the teaching of U.S. Pat. No. 3,516,846 are not discrete microcapsules, but agglomerates of sponge-like consistency having a substantially greater particle size and a markedly greater particle weight. These properties result in a high sedimentation rate of the agglomerates, which is particularly inexpedient for formulating and storing spray mixtures. In addition, the rate of release of the active ingredient, or decomposition rate of the particles, cannot be satisfactorily controlled, as—owing to the spongy structure of differing agglomerate size—the size and surface of the particles cannot be determined with exactitude.

It is therefore the object of this invention to provide a pesticidal formulation using a urea/formaldehyde precondensate, the active ingredient carrier being in the form of discrete microcapsules of defined surface and particle size.

Surprisingly, it has now been found that a change in the molar ratio of urea to formaldehyde results not in the formation of the agglomerates disclosed in U.S. Pat. No. 3,516,846, but in the formation of discrete microcapsules of defined particle size which are eminently suitable for the preparation of pesticidal formulations.

Accordingly, the invention postulates the preparation of microcapsules by stirring an aqueous solution of a precondensate of urea and formaldehyde, in the molar ratio of 1:2.7 to 1:3.5, into an acidified aqueous dispersion of a water-immiscible pesticide or of a readily volatile solvent.

The use of an aqueous dispersion of substantially non-volatile or solid pesticides in the process of this invention results in the formation of discrete microcapsules which contain the pesticide. The use of an aqueous dispersion of a readily volatile solvent leads to the formation of microcapsules which contain the readily volatile solvent. The solvent can be removed from these capsules in simple manner, conveniently by fluidised bed drying. The hollow microcapsules so obtained are admirably suitable for encapsulating liquid or low-melting pesticides. All that is required to encapsulate the pesticides is to mix the liquid pesticide with the hollow capsules. The pesticide penetrates the capsule wall and fills out the hollow capsule. The inventive process is also particularly suitable for encapsulating water-soluble pesticides which it has not been possible to encapsulate by standard methods most of which start from dispersions or emulsions of the pesticide in water. The invention also relates to microcapsules which are prepared by the above described process.

The invention further relates to pesticidal formulations in the form of microcapsules having a capsule wall made from a urea/formaldehyde polycondensate and prepared by the above described novel process, as well as to a process for controlling weeds, plant diseases, insects and representatives of the order Acarina, which process comprises applying a pesticidally effective amount of a formulation containing the novel microcapsules to said plants, insects and representatives of the order Acarina or to the loci thereof.

A molar ratio of urea to formaldehyde of 1:2.8 to 1:3.3 is particularly advantageous for the preparation of the precondensate. A molar ratio of urea to formaldehyde of 1:2.9 to 1:3.1 is especially preferred.

The preparation of the precondensate is carried out under basic conditions, preferably in the pH range from 7 to 10, most preferably from 7.5 to 9.5. The adjustment of the pH is not critical and may typically be made with aqueous sodium hydroxide. The preparation of the precondensate can be carried out in the temperature range from 25° to 90° C., preferably from 50° to 70° C. The reaction takes place over 10 to 120 minutes, the preferred reaction time being from 30 to 60 minutes.

The precondensates are storage stable and are preferably stored at temperatures below +10° C.

Normally any water-soluble acid may be used for acidifying the aqueous dispersion. Very suitable acids are typically formic acid, acetic acid, citric acid, hydrochloric acid, sulfuric acid or phosphoric acid. It is preferred to use citric acid or hydrochloric acid. The pH of the aqueous dispersion is preferably in the range from 1 to 3.

If a pesticide is used for the aqueous dispersion, then preferably it will be a herbicide, preferably selected from the class of the ureas, sulfonyl ureas, chloroacetanilides or triazines, an insecticide or acaricide, preferably selected from the class of the thioureas, or a fungicide, preferably selected from the class of the anilinopyrimidine derivatives.

Exemplary of suitable herbicides are: piperophos, metolachlor, pretilachlor, chlortoluron, terbuthylazine, terbutryn, dimethametryn, isoproturon, atrazine, simazine, fenclorim, triasulfuron, primisulfuron, cinosulfuron and 3-(6-methoxy-4-methyl-1,3,5-triazin-2-yl)-1-[2-(3,3,3-trifluorpropyl)phenylsulfonyl]urea.

Exemplary of suitable insecticides and acaracides are bromopropylate, cypermethrin, dichlorphos, isazofos, methidathion, profenofos, diazinon, and furathiocarb and diafenthiuron.

Exemplary of suitable fungicides are metalaxyl, pyroquilon, penconazol, fenpiclonil, propiconazol, 2-phenylamino-4-methyl-6-cyclopropylpyrimidine and difenconazol.

If a readily volatile solvent is used for the aqueous dispersion, then preferred organic solvents are aliphatic or aromatic hydrocarbons or mixtures thereof. Particularly preferred solvents are pentane, isopentane, hexane, heptane, cyclohexane, methylcyclohexane, benzene, diethyl ether, dibutyl ether, tetrahydrofuran or white spirit.

Suitable pesticides for encapsulating in hollow capsules in the preparation of which a readily volatile solvent has been used are liquid or low-melting pesticides such as the herbicides piperophos, metolachlor and pretilachlor, the insecticides and acaricides dichlorphos, phosphamidon, monocrotophos (low-melting), isazofos, methidathion (low melting), profenofos, diazinon and furathiocarb (low-melting), and the fungicides propiconazol and 2-phenylamino-4-methyl-6-cyclopropylpyrimidine.

The wall thickness of the microencapsulated pesticide is controlled by the ratio of pesticide to the amount of precondensate. The wall thickness of the hollow capsules is controlled by the ratio of the organic phase to the amount of precondensate.

The particle size of the microcapsules is governed by the particle size of the dispersed phase. The particle diameter of the dispersed phase is correlated in turn to the stirring speed. By varying the stirring speed for dispersing the dispersed phase it is thus possible to influence the particle diameter. High stirring speeds are necessary to obtain small particle diameters. The particle size can depend on the stirring speed, type of stirrer and reactor, as well as on the physicochemical conditions, and must in the individual case be determined for the respective reaction (type of stirrer, stirring volume, viscosity of the solution and the like). The rule of thumb is that the rotation speed of the stirrer will typically be 3–16, preferably 4–8 m/sec, measured at the farthest point to the axis of rotation of the stirrer. The particle diameter is normally in the range from 1 to 100 µm, the preferred range being from 1 to 50 µm.

The following non-limitative Examples illustrate the invention in more detail.

WORKING EXAMPLES

Example 1

Preparation of a Precondensate

With stirring, 20 g (0.33 mol) of urea are dissolved in 100 g (1 mol) of a 30% aqueous solution of formaldehyde. After adjusting the pH to 8.5–9.5 with 1N aqueous sodium hydroxide, the solution is heated to 70° C. and stirred for 10 to 60 minutes at this temperature. The solution is thereafter cooled to room temperature.

Example 2

Preparation of a Hollow Capsule 200 ml of water, 100 ml of white spirit and 15 ml of 37% aqueous hydrochloric acid are charged to a stirred reactor and efficiently stirred with a dispersing stirrer. Then the precondensate prepared in Example 1 is added at constant stirring intensity. After 10–15 minutes, the precondensate has precipitated to form spherical particles on the surface of the dispersed liquid droplets. A suspension of microcapsules which contains white spirit is obtained. After evaporation of the solvent by suction filtration and subsequent drying, these microcapsules form hollow capsules with a diameter of 10 to 150 µm which are suitable for the sorption of liquid pesticides. If desired, the suspension can be stirred for 60–90 minutes after addition of the precondensate; but in that case the shear of the stirrer is correspondingly reduced.

Example 3

Microcapsules Containing Atrazine (4-ethylamino-2-chloro-6-isopropylamino-1,3,5-triazine)

In a stirred reactor, 200 ml of water, 50 g of atrazine and 100 ml of the precondensate prepared in Example 1 are intensively mixed with a stirrer. Then, at constant stirring intensity, 0.15 mol of aqueous hydrochloric acid (32% by weight) is rapidly added. The mixture is stirred for 60 minutes to give an aqueous dispersion of microcapsules which contain atrazine and which can be formulated direct or, after suction filtration, subjected to a drying process at a temperature of 130° C.

Examples 4 and 5

In accordance with the procedure of Example 2, microcapsules of comparable quality are obtained with 0.05 and 0.015 mol, respectively, of aqueous hydrochloric acid (32% by weight) instead of 0.15 mol of aqueous hydrochloric acid (32% by weight).

Example 6

Microcapsules containing triasulfuron 3-(6-methoxy-4-methyl-1,3,5-triazin-2-yl)-1-[2-(2-chloroethoxy)phenylsulfonyl]urea In a stirred reactor, 200 ml of water, 50 g of triasulfuron and 100 ml of the precondensate prepared in Example 1 are intensively mixed with a stirrer. Then, at constant stirring intensity, 0.05 mol of aqueous hydrochloric acid (32% by weight) is rapidly added. The mixture is stirred for 60 minutes to give an aqueous dispersion of microcapsules which contain triasulfuron and which can be formulated direct or, after suction filtration, subjected to a drying process at a temperature of 130° C.

Example 7

Microcapsules Containing 3-(6-methoxy-4-methyl-1,3,5-triazin-2-yl)-1-[2-(3-trifluoropropyl) phenylsulfonyl]urea In a stirred reactor, 200 ml of water, 50 g of 3-(6-methoxy-4-methyl-1,3,5-triazin-2-yl)-1-[2-(3-trifluoropropyl) phenylsulfonyl]urea and 100 ml of the precondensate prepared in Example 1 are intensively mixed with a stirrer. Then, at constant stirring intensity, 0.15 mol of aqueous hydrochloric acid (32% by weight) is rapidly added. The mixture is stirred for 60 minutes to give an aqueous dispersion of microcapsules which contain 3-(6-methoxy-4-methyl-1,3,5-triazin-2-yl)- 1-[2-(3-trifluoropropyl) phenylsulfonyl]urea and which can be formulated direct or, after suction filtration, subjected to a drying process at a temperature of 130° C.

Example 8

Microcapsules Containing 2-phenylamino-4-methyl-6-cyclopropylpyrimidine

In a stirred reactor, 200 ml of water, 50 g of 2-phenylamino-4-methyl-6-cyclopropylpyrimidine and 100 ml of the precondensate prepared in Example 1 are intensively mixed with a stirrer. Then, at constant stirring intensity, 0.15 mol of aqueous hydrochloric acid (32% by weight) is rapidly added. The mixture is stirred for 60 minutes to give an aqueous dispersion of microcapsules which contain 2-phenylamino-4-methyl-6-cyclopropylpyrimidine and which can be formulated direct or, after suction filtration, subjected to a drying process at a temperature of 130° C.

Microcapsules of urea and formaldehyde can be prepared in particularly simple manner by the process of this invention. A particular advantage of the novel process is that no additional dispersants are needed to prepare the microcapsules.

What is claimed is:

1. A process for the preparation of microcapsules by rapidly stirring an aqueous solution of a precondensate of urea and formaldehyde, in the molar ratio of 1:3.0 to 1:3.5, into an acidified aqueous dispersion of a water-immiscible herbicide.

2. A process according to claim 1, wherein the molar ratio of urea to formaldehyde is 1:3.0 to 1:3.3.

3. A process according to claim 1, wherein the molar ratio of urea to formaldehyde is 1:3.0 to 1:3.1.

4. A process according to claim 1, wherein the herbicide is selected from the group consisting of ureas, sulfonyl ureas, chloroacetanilides and triazines.

* * * * *